United States Patent
Superak

(10) Patent No.: US 6,414,224 B1
(45) Date of Patent: Jul. 2, 2002

(54) PUMPKIN VARIETY ZYD5B

(75) Inventor: Theodore H. Superak, Davis, CA (US)

(73) Assignee: Harris Moran Seed Company, Modesto, CA (US)

( * ) Notice: Subject to any disclaimer, the term of this patent is extended or adjusted under 35 U.S.C. 154(b) by 0 days.

(21) Appl. No.: 09/562,457

(22) Filed: May 2, 2000

(51) Int. Cl.$^7$ .............................. A01H 1/00; A01H 5/00; A01H 5/10; A01H 4/00; C12N 5/04

(52) U.S. Cl. ........................ 800/310; 800/260; 800/278; 435/420; 435/430; 435/430.1

(58) Field of Search ................................ 800/310, 260, 800/265, 266, 267, 274, 278, 300, 301, 302; 435/421, 430, 430.1, 420

(56) References Cited

U.S. PATENT DOCUMENTS

| | | | | |
|---|---|---|---|---|
| 5,777,196 A | * | 7/1998 | Hall | 800/200 |
| 5,811,642 A | * | 9/1998 | Stracheljahn | 800/200 |
| 5,948,957 A | * | 9/1999 | Chapko et al. | 800/320.1 |
| 5,969,212 A | * | 10/1999 | Getschman | 800/200 |

OTHER PUBLICATIONS

Howden Large Pumpkin. Harris Moran Seed Company Online Database. Version 26 Sep. 2001. http://www.harris-moran.com/products/pumpkin.*

Katavic, V. et al., "Host–tissue differences in transformation of pumpkin (Cucurbita pepo L.) by Agrobacterium rhizogenes." 1991, Plant Cell Tissue and Organ Culture, vol. 24, pp. 35–42.* di Toppi. L. S. et al., "Cucurbita pepo L. can be transformed by Agrobacterium rhizogenes." 1997, Plant Cell Tissue and Organ Culture, vol. 51, pp. 89–93.*

Rakoczy–Trojanowska, M. and Malepszy, "A mehtod for increased plant regeneration from immature F1 and BC1 embryos of Cucurbita maxima Duch. x C. pepo L. hybrids." 1989, Plant Cell, Tissue and Organ Culture, vol. 18, pp. 191–194.*

Keinath, A. P. and DuBose, V. B. "Evaluation of Pumpkin Cultivars for Powdery and Downy Mildew Resistance, Virus Tolerance, and Yield." 2000, HortScience, vol. 35, pp. 281–285/*

Zhang, X. P. et al., "Development of Genic Male–sterile Watermelon Lines with Delayed–green Seedling Marker."1996, HortScience, vol. 31, pp. 123–126.*

Bennetzen, J. L. and Jones, J. D. G. "Approaches and Progress in the Molecular Cloning of Plant Disease Resistance Genes." 1992, Genetic Engineering, vol. 14, pp. 99–124.*

De Bolle, M. F. C. et al., "Antimicrobial peptides from Mirabilis jalapa and Amaranthus caudatus: expression, processing, localization and biological activity n transgenic tobacco." 1996, Plant Molecular Biology, vol. 31, pp. 993–1008.*

Pang, S. et al., "Expression of a gene encoding a scorpion insectotoxin peptide in yeast, bacteria and plants."1992, Gene, vol. 116, pp. 165–172.*

* cited by examiner

*Primary Examiner*—David T. Fox
*Assistant Examiner*—Francis P. Moonan
(74) *Attorney, Agent, or Firm*—Rothwell, Figg, Ernst & Manbeck

(57) ABSTRACT

A novel pumpkin variety, designated ZYD5B, is disclosed. The invention relates to the seeds of pumpkin variety ZYD5B, to the plants of pumpkin variety ZYD5B and to methods for producing a pumpkin plant produced by crossing the variety ZYD5B with itself or another pumpkin line. The invention further relates to hybrid pumpkin seeds and plants produced by crossing the variety ZYD5B with another pumpkin line.

27 Claims, No Drawings

PUMPKIN VARIETY ZYD5B

BACKGROUND OF THE INVENTION

The present invention relates to a new and distinctive pumpkin variety, designated ZYD5B. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, tolerance to drought and heat, and better quality.

Choice of breeding or selection methods depends on the mode of plant reproduction, the heritability of the trait(s) being improved, and the type of cultivar used commercially (e.g., $F_1$ hybrid, variety, etc.). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s). The best lines are candidates for new commercial cultivars; those still deficient in a few traits are used as parents to produce new populations for further selection.

These processes, which lead to the final step of marketing and distribution, usually take from ten to 30 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior pumpkin varieties and hybrids. The breeder initially selects and crosses two or more parental lines, followed by repeated selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same pumpkin traits.

Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same variety twice by using the exact same original parents and the same selection techniques. This unpredictability results in the expenditure of large research monies to develop superior new pumpkin varieties.

The development of commercial pumpkin hybrids requires the development of varieties, the crossing of these varieties, and the evaluation of the crosses. Pedigree breeding and recurrent selection breeding methods are used to develop varieties from breeding populations. Breeding programs combine desirable traits from two or more varieties or various broad-based sources into breeding pools from which varieties are developed by crossing and selection of desired pheno-types. The new varieties are crossed with other varieties and the hybrids from these crosses are evaluated to determine which have commercial potential.

Pedigree breeding is used commonly for the improvement of both self-pollinating and cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987, Basset, 1986).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the varieties that give the best hybrid performance have been identified, the hybrid seed can be reproduced indefinitely as long as the homogeneity of the parent is maintained. A single-cross hybrid is produced when two varieties are crossed to produce the $F_1$ progeny. Much of the hybrid vigor exhibited by $F_1$ hybrids is lost in the next generation ($F_2$).

Pumpkin is an important and valuable crop. Thus, a continuing goal of plant breeders is to develop stable, high yielding pumpkins that are agronomically sound. The reasons for this goal are obviously to maximize the total yield and quality produced on the land used. To accomplish this goal, the pumpkin breeder must select and develop pumpkin plants that have the traits that result in superior varieties and hybrids.

SUMMARY OF THE INVENTION

According to the invention, there is provided a novel pumpkin variety, designated ZYD5B. This invention thus relates to the seeds of pumpkin variety ZYD5B, to the plants of pumpkin variety ZYD5B and to methods for producing a pumpkin plant produced by crossing the variety ZYD5B with itself or another pumpkin variety. This invention further relates to hybrid pumpkin seeds and plants produced by crossing the variety ZYD5B with another pumpkin variety.

DETAILED DESCRIPTION OF THE INVENTION

Pumpkin variety ZYD5B is a winter pumpkin of the species pepo with superior characteristics. Pumpkin variety ZYD5B was developed in two steps: (1) by creation of a recurrent parent and (2) by backcrossing disease resistance and bush habit into this recurrent parent.

(1) The recurrent parent was created by selecting open pollinated fruit in an isolation of Howden pumpkin and then using single plant pedigree selection to develop true breeding lines. Two closely related lines were developed that were involved in the backcrossing. Recurrent parent D13 was developed by selecting a single open pollinated fruit from the isolation and then selfing for 5 generations. Recurrent parent D5 was developed the same way except that another selection was chosen in the second self generation, and this was selfed for one additional generation.

(2) The donor of the Zucchini Yellow Mosaic Virus (ZYMV) resistance, Powdery Mildew (PM) resistance, and bush habit was a gray zucchini summer squash designated ZY5. The initial cross of this parent to pumpkin was made to an individual plant of a segregating population designated QBDNTt2. The first cross to the described recurrent parent was made to D13. There were 3 additional successive backcrosses, these being to D5. Six generations of single plant pedigree selection were made before the first open pollinated cage increase. Plants resistant to ZYMV and PM and having a bushy habit were selected at each segregating generation.

VARIETY DESCRIPTION INFORMATION

Winter Pumpkin
    Genus: Cucurbita
    Species: Pepo
    A. Plant: Semi-bush
    prickly
    B. Main Stem: Angled
    Average length (cm): 337
    Diameter at midpoint of first internode (mm): 35
    Average number of internodes: 45
    C. Leaves:
    Shape: Reniform; shallow lobed
    Margin: Dentate, flat
    Width (cm): 35
    Length (cm): 43
    Surface: smooth
    Dorsal surface: soft hairy
    Ventral surface: bristled
    Color: Medium green, not blotched
    Petiole length (cm): 40
    D. Flower—Pistillate
    Diameter (cm): 20
    Ovary: Drum-like
    Pedicel length (cm): 3
    Margin: curved, plain
    Sepals width (mm): 1 Length (mm): 10
    Color: deep yellow
    E. Flower—staminate:
    Sepals: width (mm): 3 Length (mm): 32
    Pedicil length (cm): 20
    Color: deep yellow
    F. Fruit:
    Length (cm): 27.3
    Width (cm) stem end: 28
    Width (cm) blossom end: 27.5
    Average weight (gm): 7,952
    Shape according to variety type: Connecticut Field
    Apex: depressed
    Base: depressed
    Ribs: prominent
    Rib furrows: Medium deep, medium wide
    Fruit surface: smooth
    Warts: none
    Blossom scar button: depressed G. Rind:
Thickness at medial (mm): 1
Rind: hard
Color pattern: regular, orange
H. Flesh:
Thickness: Blossom end (mm): 39.8
   Medial (mm): 40.2
   Stem end (mm): 38.4
Texture: granular, firm, moist
Flavor: insipid
Quality: good
Color: cream
I. Seed Cavity (sectioned apex to base)
Length (cm): 19.1
Width (cm): 20.1
Location: conforms to fruit shape
Placental Tissue: sparse
Center core: inconspicuous
J. Fruit Stalks: Irregular, not Twisted, Tapered, Slightly Curved
   Length (cm): 8.6
   Diameter (cm): 2.9
   Texture: hard
   Farrows: deep
   Surface: spiney
   Attachment end: expanded
   Detaches: with difficulty
   Color: medium green
K. Seeds
   Length (mm): 18.1
   Width (mm): 10.3
   Thickness (mm): 2.5
   Face Surface: Smooth
   Color: Cream
   Luster: Dull
   Margin: Straight, rounded
   Separation from pulp: easy
   Grams per 100 seeds: 15
   No. seeds perfruit: 332
   Yield: 3 fruits per plant This invention is also directed to methods for producing a pumpkin variety by crossing a first parent pumpkin variety with a second parent pumpkin variety, wherein the first or second pumpkin variety is the pumpkin plant from the variety ZYD5B. Further, both first and second parent pumpkin plants may be from the variety ZYD5B. Therefore, any methods using the pumpkin variety ZYD5B are part of this invention; including selfing, backcrosses, hybrid breeding, and crosses to populations. Any plants produced using pumpkin variety ZYD5B as a parent are within the scope of this invention. Advantageously, the pumpkin variety is used in crosses with other pumpkin varieties to produce first generation ($F_1$) hybrid seed and plants with superior characteristics.

As used herein, the term "plant" includes plant cells, plant protoplasts, plant cell of tissue culture from which pumpkin plants can be regenerated, plant calli, plant clumps, and plant cells that are intact in plants or parts of plants, such as pollen, flowers, seeds, leaves, stems, and the like.

The closest prior variety to ZYD5B is the pumpkin variety Howden. While similar, there are numerous differences including the unique characteristics of ZYD5B's resistance to ZYMV and PM and bushy habit. The value of ZYD5B is in its use as a parent in $F_1$ hybrids. Hybrids made with ZYD5B are expected to have (1) tolerance to ZYMV, PM and possibly to other related viruses (WMV and PRSV); (2) a bush plant habit; (3) attractive pumpkin fruits with well defined ribs deep orange skin color, full round shape, and large dark green fruit stalks; and (4) high yield.

TABLES

In the table that follows, the traits and characteristics of pumpkin variety HMX9697, a hybrid between ZYD5B and another pumpkin inbred, ZYB24B, is presented for the key characteristics and traits. Information about HMX9697, as compared to several check varieties is presented.

In Table 1 HMX9697 is compared to other pumpkin varieties at a variety trial conducted at the Kansas State University. Information for the different varieties includes:

In column 1 (Variety) the variety names are listed.

In column 2 (#/Acre) the number of pumpkins per acre grown in a particular plot are given.

In column 3 (Lb/Acre) the pounds of pumpkin fruit per acre are listed.

In column 4 (Lb/Pumpkin) the average pounds of the number of pumpkins grown in that variety's particular plot.

In column 5 (Color) the color of the fruit is listed. DO=dark orange, MO=medium orange, BO=bright orange and VDO=very dark orange.

In column 6 (Surface) the pumpkin surface is listed as ribbed (Rib), slightly ribbed (SI Rib) or smooth (Smooth).

In column 7 (Stem Color) the color of the stem is listed. DG=dark green and MG=medium green.

In column 8 (Stem Size) the stem sizes are rated as either excellent, good, fair or poor.

TABLE 1

1999 Pumpkin Variety Trial
Kansas State University, Olathe Research and Extension Center

| Variety | #/Acre | Lb/Acre | Lb/Pumpkin | Color | Surface | Stem Color | Stem Size |
|---|---|---|---|---|---|---|---|
| Conn Field | 2969 | 41253 | 13.90 | DO | Rib | DG | Good |
| HMX9697 | 2526 | 24195 | 9.58 | DO | SI Rib | DG | Exc. |
| Howden | 1258 | 19853 | 15.78 | DO | Rib | DG | G/Exc |
| Merlin | 1968 | 19328 | 9.82 | VDO | SI Rib | DG | Good |
| Howden Biggie | 1065 | 14652 | 13.76 | DO | Rib | DG | Exc. |
| HMX6688 | 2468 | 10602 | 4.30 | VDO | SI Rib | DG | Exc. |

When the term inbred pumpkin plant is used in the context of the present invention, this also includes any single gene conversions of that inbred. The term single gene converted plant as used herein refers to those pumpkin plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental pumpkin plants for that inbred. The parental pumpkin plant which contributes the gene for the desired characteristic is termed the nonrecurrent or donor parent. This terminology refers to the fact that the nonrecurrent parent is used one time in the backcross protocol and therefore does not recur. The parental pumpkin plant to which the gene or genes from the nonrecurrent parent are transferred is known as the recurrent parent as it is used for several rounds in the backcrossing protocol (Poehiman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a pumpkin plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, corn endosperm, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

A further aspect of the invention relates to tissue culture of pumpkin plants designated ZYD5B. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, leaves, stalks, roots, root tips, anthers, and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as flesh or fruit, has been used to produce regenerated plants. (See U.S. Pat. Nos. 5,677,157; 5,445,961; 5,322,789; 5,948,957 and 5,969,212, the disclosures of which are incorporated herein by reference).

DEPOSIT INFORMATION

A deposit of the Harris Moran Seed Company pumpkin variety ZYD5B disclosed above and recited in the appended claims has been made with the American Type Culture Collection (ATCC), 10801 University Boulevard, Manassas, Va. 20110. The date of deposit was Feb. 12, 2002. The deposit of 2,500 seeds were taken from the same deposit maintained by Harris Moran Seed Company since prior to the filing date of this application. All restrictions upon the deposit have been removed, and the deposit is intended to meet all of the requirements of 37 C.F.R. § 1.801–1.809. The ATCC accession number is PTA-4064. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A pumpkin seed designated ZYD5B, a sample of said seed having been deposited under ATCC Accession No. PTA-4064.

2. A pumpkin plant, or parts thereof, produced by growing the seed of claim 1.

3. Pollen of the plant of claim 2.

4. An ovule of the plant of claim 2.

5. A pumpkin plant, or parts thereof, having all of the physiological and morphological characteristics of the pumpkin plant of claim 2.

6. A tissue culture of regenerable cells of a pumpkin plant of inbred line ZYD5B, wherein the tissue regenerates plants capable of expressing all the morphological and physiological characteristics of the inbred line ZYD5B.

7. A tissue culture according to claim 6, the cells being from a tissue selected from the group consisting of leaves, pollen, embryos, roots, root tips, anthers, flowers, stalks and fruit.

8. A pumpkin plant regenerated from the tissue culture of claim 6, capable of expressing all the morphological and physiological characteristics of inbred line ZYD5B.

9. A method for producing a hybrid pumpkin seed comprising crossing a first inbred parent pumpkin plant with a second inbred parent pumpkin plant and harvesting the resultant hybrid pumpkin seed, wherein said first or second parent pumpkin plant is the pumpkin plant of claim 2.

10. A hybrid pumpkin seed produced by the method of claim 9.

11. A hybrid pumpkin plant, or parts thereof, produced by growing said hybrid pumpkin seed of claim 10.

12. Pumpkin seed produced by growing said hybrid pumpkin plant of claim 11.

13. A pumpkin plant, or parts thereof, produced from seed of claim 12.

14. A method for producing a hybrid pumpkin seed comprising crossing an inbred plant according to claim 2 with another, different pumpkin plant.

15. A hybrid pumpkin seed produced by the method of claim 14.

16. A hybrid pumpkin plant, or its parts, produced by growing said hybrid pumpkin seed of claim 15.

17. Pumpkin seed produced from said hybrid pumpkin plant of claim 16.

18. A pumpkin plant, or its parts, produced from the pumpkin seed of claim 17.

19. A method for producing a ZYD5B-derived pumpkin plant, comprising:
  a) crossing inbred pumpkin line ZYD5B, a sample of seed of said line having been deposited under ATCC Accession No. PTA-4064, with a second pumpkin plant to yield progeny pumpkin seed;
  b) growing said progeny pumpkin seed, under plant growth conditions, to yield said ZYD5B-derived pumpkin plant.

20. The method of claim 19, further comprising:
  c) crossing said ZYD5B-derived pumpkin plant with itself or another pumpkin plant to yield additional ZYD5B-derived progeny pumpkin seed;
  d) growing said progeny pumpkin seed of step (c) under plant growth conditions, to yield additional ZYD5B-derived pumpkin plants;
  e) repeating the crossing and growing steps of (c) and (d) from 0 to 7 times to generate further ZYD5B-derived pumpkin plants.

21. The method of claim 19, still further comprising utilizing plant tissue culture methods to derive progeny of said ZYD5B-derived pumpkin plant.

22. The pumpkin plant, or parts thereof, of claim 2, wherein the plant or parts thereof have been transformed so that its genetic material contains one or more transgenes operably linked to one or more regulatory elements.

23. A method for producing a pumpkin plant that contains in its genetic material one or more transgenes, comprising crossing the pumpkin plant of claim 22 with either a second plant of another pumpkin line, or a non-transformed pumpkin plant of the line ZYD5B, so that the genetic material of the progeny that result from the cross contains the transgene(s) operably linked to a regulatory element.

24. Pumpkin plants, or parts thereof, produced by the method of claim 23.

25. A method for developing a pumpkin plant in a pumpkin plant breeding program using plant breeding techniques which include employing a pumpkin plant, or its parts, as a source of plant breeding material comprising: using the pumpkin plant, or its parts, of claim 2 as a source of said breeding material.

26. The pumpkin plant of claim 5, further comprising a single gene conversion.

27. The single gene conversion pumpkin plant of claim 26, where the gene is selected from the group consisting of: a transgene, a dominant allele, and a recessive allele.

* * * * *